(12) United States Patent
Lednev et al.

(10) Patent No.: US 8,467,053 B2
(45) Date of Patent: Jun. 18, 2013

(54) IDENTIFICATION OF BODY FLUIDS USING RAMAN SPECTROSCOPY

(75) Inventors: Igur K. Lednev, Glenmont, NY (US); Kelly Virkler, Albany, NY (US)

(73) Assignee: The Research Foundation of State University of New York, Albany, NY (US)

( * ) Notice: Subject to any disclaimer, the term of this patent is extended or adjusted under 35 U.S.C. 154(b) by 76 days.

(21) Appl. No.: 12/994,735

(22) PCT Filed: Jun. 2, 2009

(86) PCT No.: PCT/US2009/045955
§ 371 (c)(1),
(2), (4) Date: Feb. 23, 2011

(87) PCT Pub. No.: WO2009/149072
PCT Pub. Date: Dec. 10, 2009

(65) Prior Publication Data
US 2011/0143961 A1   Jun. 16, 2011

Related U.S. Application Data

(60) Provisional application No. 61/058,412, filed on Jun. 3, 2008, provisional application No. 61/149,566, filed on Feb. 3, 2009.

(51) Int. Cl.
*G01J 3/44* (2006.01)
*G01J 3/00* (2006.01)
*G01N 21/65* (2006.01)
*G01N 21/00* (2006.01)

(52) U.S. Cl.
USPC ............ 356/301; 356/300; 356/928; 356/952

(58) Field of Classification Search
USPC .............................................. 506/13; 356/301
See application file for complete search history.

(56) References Cited

U.S. PATENT DOCUMENTS

| 5,515,847 A | 5/1996 | Braig et al. |
| 5,553,616 A | 9/1996 | Ham et al. |
| 5,751,415 A | 5/1998 | Smith et al. |

(Continued)

FOREIGN PATENT DOCUMENTS

| JP | 09079982 A | 3/1997 |
| WO | 2007/089551 A2 | 8/2007 |

OTHER PUBLICATIONS

Edwards et al, Diagnostic Raman spectroscopiy for the forensic detection of biomaterials and the preservation of cultural heritage, Anal Bioanal Chem (2005) 382:1398-1406.*

(Continued)

*Primary Examiner* — Samuel Woolwine
*Assistant Examiner* — Kaijiang Zhang
(74) *Attorney, Agent, or Firm* — LeClairRyan, a Professional Corporation (57) ABSTRACT

The present invention relates to a method of identifying types of body fluids in a sample. This method involves providing a sample potentially containing one or more types of body fluids. The sample is subjected to Raman spectroscopy to produce a Raman spectroscopic signature for the sample. The Raman spectroscopy signature is identified to ascertain the types of body fluids in the sample. A method of establishing a reference Raman spectroscopic signature for specific types of body fluids is also disclosed as is a library of such reference signatures is also disclosed.

20 Claims, 6 Drawing Sheets

U.S. PATENT DOCUMENTS

| | | | |
|---|---|---|---|
| 5,796,476 A * | 8/1998 | Wang et al. ............... 356/301 |
| 5,958,780 A | 9/1999 | Asher et al. |
| 6,064,897 A | 5/2000 | Lindberg et al. |
| 6,151,522 A | 11/2000 | Alfano et al. |
| 6,226,082 B1 | 5/2001 | Roe |
| 6,560,478 B1 | 5/2003 | Alfano et al. |
| 6,642,012 B1 | 11/2003 | Ashdown |
| 6,868,285 B2 | 3/2005 | Muller-Dethlefs |
| 7,271,896 B2 | 9/2007 | Chan et al. |
| 7,651,851 B2 | 1/2010 | Clarke et al. |
| 2002/0093651 A1 | 7/2002 | Roe |
| 2005/0084063 A1 | 4/2005 | Heismann et al. |
| 2005/0148098 A1 | 7/2005 | Su et al. |
| 2006/0035234 A1 | 2/2006 | Henderson et al. |
| 2006/0240401 A1 | 10/2006 | Clarke et al. |
| 2007/0224683 A1 | 9/2007 | Clarke et al. |
| 2007/0240505 A1 | 10/2007 | Cammarata et al. |

OTHER PUBLICATIONS

PCT KIPO International Search Report and Written Opinion for PCT/US2009/045955, Jan. 13, 2010.

Brody et al., "Chemometric Methods Applied to the Differentiation of Fourier-Transform Raman Spectra of Ivories," Analytica. Chimica. Acta. 427:223-232 (2001).

Berger et al., "Multicomponent Blood Analysis by Near-Infrared Raman Spectroscopy," Appl. Optic. 38(13):2916-2926 (1999) (Abstract only).

* cited by examiner

IDENTIFICATION OF BODY FLUIDS USING RAMAN SPECTROSCOPY

This application claims the benefit of U.S. Provisional Patent Application Ser. Nos. 61/058,412, filed Jun. 3, 2008, and 61/149,566, filed Feb. 3, 2009, which are hereby incorporated by reference in their entirety.

FIELD OF THE INVENTION

The present invention relates to the identification of body fluids using Raman spectroscopy.

BACKGROUND OF THE INVENTION

The identification of body fluids and stains discovered at a crime scene is a major part of forensic investigation today. The three most common fluids found are blood, semen, and saliva, and there are several methods used currently to distinguish one from another. Blood can be presumptively tested for using different color spot tests, but these tests are destructive to the sample and can also have false positives (Siegel, J. A., Ed., "Encyclopedia of Forensic Sciences," Academic Press, San Diego (2000)). If only a small amount of sample is available, careful decisions must be made as to whether the presumptive test is necessary. There are also confirmatory tests for blood that conclusively prove blood is present, and some of these tests can distinguish between species. Semen is similar in that there are destructive presumptive tests as well as confirmatory tests. Saliva, however, has no confirmatory tests. Therefore, an examiner can never be positive about the presence of saliva (Siegel, J. A., Ed., "Encyclopedia of Forensic Sciences," Academic Press, San Diego (2000)). Most presumptive tests can be performed in the field, but some sample preparation such as extraction is often necessary. Most confirmatory tests must be done in the laboratory, so forensic experts responding at a crime scene will not know the confirmed identity of fluid traces until much later on. The main problem with these tests is the destruction of the sample. Sometimes a case can be broken with just the smallest amount of biological evidence, so it is crucial that these small quantities are examined as efficiently as possible and nondestructively at the crime scene. Another issue is the ambiguity of the tests. Current simple in-field screening tests do not confirm the presence of a particular fluid, and saliva can never be confirmed. Finally, mixtures of fluids are frequently found, and this can make identification and subsequent DNA analysis even more difficult. The forensic community is in great need of a reliable and ultimately in-field method that can exclusively distinguish between the common and uncommon body fluids, as well as not destroy the sample in the process.

Raman spectroscopy is a technique that is increasing in popularity among the different disciplines of forensic science. Some examples of its use today involve the identification of drugs (Hodges et al., "The Use of Fourier Transform Raman Spectroscopy in the Forensic Identification of Illicit Drugs and Explosives," *Molecular Spectroscopy* 46:303-307 (1990)), lipsticks (Rodger et al., "The In-Situ Analysis of Lipsticks by Surface Enhanced Resonance Raman Scattering," *Analyst* 1823-1826 (1998)), and fibers (Thomas et al., "Raman Spectroscopy and the Forensic Analysis of Black/Grey and Blue Cotton Fibres Part 1: Investigation of the Effects of Varying Laser Wavelength," *Forensic Sci. Int.* 152:189-197 (2005)), as well as paint (Suzuki et al., "In Situ Identification and Analysis of Automotive Paint Pigments Using Line Segment Excitation Raman Spectroscopy: I. Inorganic Topcoat Pigments," *J. Forensic Sci.* 46:1053-1069 (2001)) and ink (Mazzella et al., "Raman Spectroscopy of Blue Gel Pen Inks," *Forensic Sci. Int.* 152:241-247 (2005)) analysis. The theory behind Raman spectroscopy is based on the inelastic scattering of low-intensity, nondestructive laser light by a solid, liquid or gas sample. Very little or no sample preparation is needed, and the required amount of tested material could be as low as several picograms or femtoliters ($10^{-12}$ gram or $10^{-15}$ liter, respectively). A typical Raman spectrum consists of several narrow bands and provides a unique vibrational signature of the material (Grasselli et al., "Chemical Applications of Raman Spectroscopy," New York: John Wiley & Sons (1981)). Unlike infrared (IR) absorption spectroscopy, another type of vibrational spectroscopy, Raman spectroscopy shows very little interference from water (Grasselli et al., "Chemical Applications of Raman Spectroscopy," New York: John Wiley & Sons (1981)), and that makes it a great technique for analyzing body fluids and their traces. Proper Raman spectroscopic measurements do not damage the sample. The stain or swab could be tested on the field and still be available for further use in the lab for DNA analysis, and that is very important to forensic application. The design of a portable Raman spectrometer is a reality now (Yan et al., "Surface-Enhanced Raman Scattering Detection of Chemical and Biological Agents Using a Portable Raman Integrated Tunable Sensor," *Sensors and Actuators B.* 6 (2007); Eckenrode et al., "Portable Raman Spectroscopy Systems for Field Analysis," *Forensic Science Communications* 3:(2001)) which would lead to the ability to make identifications at the crime scene.

Fluorescence interference is the largest problem with Raman spectroscopy and is perhaps the reason why the latter technique has not been more popular in the past. If a sample contains molecules that fluoresce, the broad and much more intense fluorescence peak will mask the sharp Raman peaks of the sample. There are a few remedies to this problem. One solution is to use deep ultraviolet (DUV) light for exciting Raman scattering (Lednev I. K., "Vibrational Spectroscopy: Biological Applications of Ultraviolet Raman Spectroscopy," in: V. N. Uversky, and E. A. Permyakov, *Protein Structures, Methods in Protein Structures and Stability Analysis* (2007)). Practically no condensed face exhibits fluorescence below ~250 nm. Possible photodegradation of biological samples is an expected disadvantage of DUV Raman spectroscopy. Another option to eliminate fluorescence interference is to use a near-IR (NIR) excitation for Raman spectroscopic measurement. Finally, surface enhanced Raman spectroscopy (SERS) which involves a rough metal surface can also alleviate the problem of fluorescence (Thomas et al., "Raman Spectroscopy and the Forensic Analysis of Black/Grey and Blue Cotton Fibres Part 1: Investigation of the Effects of Varying Laser Wavelength," *Forensic Sci. Int.* 152:189-197 (2005)). However, this method requires direct contact with the analyte and cannot be considered to be nondestructive.

There have been other studies performed which involve the analysis of body fluids using Raman spectroscopy. SERS has been used to detect 5-fluorourcil in saliva (Farquharson et al., *J. Raman Spectrosc.* 36:208-212 (2005)), drugs in blood and urine (Trachta et al., *J. Mol. Structure* 693:174-185 (2004)), lactic acid in serum (Chiang et al., "Plasmonics: Metallic Nanostructures and Their Optical Properties III," 5927:1 Z/1-1Z/8 (2005)), and has analyzed body fluids on test strips (U.S. Patent Publication No. 2007/0224683 A1 to Clarke et al.). It has also been applied to the in vitro detection of analytes in body fluids (U.S. Patent Publication No. 2006/0240401 A1 to Clarke et al.), the detection of low levels of body fluids (Kindcade, K., *Laser Focus World* 42:109-111 (2006)), and has been used as part of a probe system to detect protein analytes (U.S. Patent Publication No. 2005/0148100 A1 to Su et al.). Many other Raman experiments not involving SERS have been conducted for detecting cancer (U.S. Patent Publication No. 2006/0170928 to Masilamani et al.), characterizing whole blood (Sato et al., *J. Biomed. Opt.* 6:366-370 (2001)), urine (Premasiri et al., *Lasers Surg. Med.* 28:330-334 (2001)), in vivo fluids (WO2006061565 to Matousek et al.), breath samples (WO2006136281 to Wolfgang), and amniotic fluid (U.S. Patent Publication No. 2006/0247536 A1 to Koski et al.). Body fluids such as urine, blood, blood plasma, blood serum, saliva, and sweat have been spiked with various components, and these components have been analyzed simultaneously by multivariate regression analysis (U.S. Pat. No. 5,796,476 to Wang et al.). One goal of the invention is to evaluate the potential use of NIR Raman spectroscopy for confirmatory analysis of body fluids for forensic purposes.

Other spectroscopic techniques have been also tested for the non-destructive analysis of body fluids. Fluorescence has been used to detect biological materials (U.S. Pat. No. 6,750, 006 to Powers et al.) and microorganisms (Estes et al, "Reagentless Detection of Microorganisms by Intrinsic Fluorescence," *Biosens. Bioelectron.* 18:511-519 (2003)). Photoluminescence has also been used in the form of a light source known as Polilight to detect stains (Jackson et al., "The Use of Polilight in the Detection of Seminal Fluid, Saliva, and Bloodstains and Comparison with Conventional Chemical-Based Screening Tests," *J. Forensic Sci.* 51(2):361-70 (2006) and *J. Forensic Sci.* 52:740-41 (2007); Stoilovic, M., "Detection of Semen and Blood Stains Using Polilight as a Light Source," *Forensic Sci. Int.* 51:289-296 (1991)), and this source has been compared to Luma-Light and Spectrum 9000 (Watkin et al., "A Comparison of the Forensic Light Sources, Polilight, Luma-Light, and Spectrum 9000," *J. Forensic Identification* 44:632 (1994)). Ultra-violet light has been used to enhance blood (Klasey et al., "Using Ultra-Violet Light to Enhance Blood," *J. Forensic Identification* 42:404 (1992)), and body secretions have been analyzed with high intensity quartz arc tubes (Auvdel M. J., "Comparison of Laser and High-Intensity Quartz Arc Tubes in the Detection of Body Secretions," *J. Forensic Sci.* 33:929-945 (1988)). It is a general advantage of Raman spectroscopy over photoluminescence in providing more specific information about the analyte. As a result, one could expect that Raman spectroscopy should offer a higher identification power when applied for body fluid identification especially in the case of mixed and contaminated samples.

Accordingly, the present invention is directed to overcoming these deficiencies in the art.

SUMMARY OF THE INVENTION

The present invention relates to a method of identifying types of body fluids in a sample. This method involves providing a sample potentially containing one or more types of body fluids. The sample is subjected to Raman spectroscopy to produce a Raman spectroscopic signature for the sample. The Raman spectroscopy signature is identified to ascertain the types of body fluids in the sample.

Another aspect of the present invention relates to a method of establishing reference Raman spectroscopic signatures for specific types of body fluids. This method involves providing known samples of specific types of body fluids. The known samples are subjected to Raman spectroscopy to produce a Raman spectroscopic signature for each known sample of a specific type of body fluid. A reference Raman spectroscopic signature is established for the specific type of body fluid based on the Raman spectroscopic signature obtained for each known sample of a specific type of body fluid subjected to Raman spectroscopy.

A further aspect of the present invention relates to a library of reference Raman spectroscopic signatures for different specific types of body fluids.

The present invention provides a method of non-destructive and confirmatory identification of body fluids. Determination of the composition of a mixed, pure, or contaminated sample of the fluids of a human or animal nature is possible with the present method. This method utilizes a minimal amount of sample in a non-destructive manner and offers the ability to perform immediate and conclusive identifications of the body fluids.

The benefits of this invention in the forensic community are significant. By the very nature of body fluid evidence, the amount of available sample is small, and the ability of Raman spectroscopy to obtain conclusive results from a very small amount is extremely valuable. This ability in combination with the non-destructive nature of the technique will allow for the subsequent DNA analysis of the sample without destroying it.

An even greater benefit of applying Raman spectroscopy to unknown body fluids will be the ability to confirm the presence of a specific fluid with one quick and simple analysis. Ultimately, the ability to perform this analysis at the scene of a crime will allow investigators to conclusively identify a fluid or even a mixture of different fluids. This will save time both on site and in the laboratory since further identification will not be necessary.

The present invention is described in Virkler et al., "Raman Spectroscopy Offers Great Potential for the Nondestructive Confirmatory Identification of Body Fluids," *Forensic Sci. Int.* 181:e1-e5 (2008) and Virkler et al., "Analysis of Body Fluids for Forensic Purposes: From Laboratory Testing to Non-Destructive Rapid Confirmatory Identification at a Crime Scene, *Forensic Sci. Int.* 188:1-17 (2009), which are hereby incorporated by reference in their entirety.

DETAILED DESCRIPTION OF THE INVENTION

The present invention relates to a method of identifying types of body fluids in a sample. This method involves providing a sample potentially containing one or more types of body fluids. The sample is subjected to Raman spectroscopy to produce a Raman spectroscopic signature for the sample. The Raman spectroscopy signature is identified to ascertain the types of body fluids in the sample.

The body fluids include, but are not limited to, blood, semen, saliva, vaginal fluid, sweat, and combinations thereof. The sample analyzed is either a solid or liquid.

The samples are identified using a Raman spectroscopy detection technique. The Raman spectroscopic signatures obtained from the samples are compared to reference Raman spectroscopic signatures for different body fluids. The signatures comparison permits the determination of the type(s) of body fluids present in the sample. The species source as well as the age range of the source of the body fluid can be determined using the method of the present invention. This permits human body fluids to be distinguished from animal body fluids.

Raman spectroscopy is a spectroscopic technique which relies on inelastic or Raman scattering of monochromatic light to study vibrational, rotational and other low-frequency modes in a system (Gardiner, D. J., *Practical Raman Spectroscopy*, Berlin: Springer-Verlag, pp. 1-3 (1989), which is hereby incorporated by reference in its entirety). Vibrational modes are very important and very specific for chemical bonds in molecules. They provide a fingerprint by which a molecule can be identified. The Raman effect is obtained when a photon interacts with the electron cloud of a molecular bond exciting the electrons into a virtual state. The scattered photon is shifted to lower frequencies (Stokes process) or higher frequencies (anti-Stokes process) as it abstracts or releases energy from the molecule. The polarizability change in the molecule will determine the Raman scattering intensity, while the Raman shift will be equal to the vibrational intensity involved.

Basic components of a Raman spectrometer are (1) an excitation source; (2) optics for sample illumination; (3) a single, double, or triple monochrometer; and (4) a signal processing system consisting of a detector, an amplifier, and an output device.

Typically, a sample is exposed to a monochromatic source usually a laser in the visible, near infrared, or near ultraviolet range. The scattered light is collected using a lens and is focused at the entrance slit of a monochromator. The monochromator which is set for a desirable spectral resolution rejects the stray light in addition to dispersing incoming radiation. The light leaving the exit slit of the monochromator is collected and focused on a detector (such as a photodiode arrays (PDA), a photomultiplier (PMT), or charge-coupled device (CCD)). This optical signal is converted to an electrical signal within the detector. The incident signal is stored in computer memory for each predetermined frequency interval. A plot of the signal intensity as a function of its frequency difference (usually in units of wavenumbers, $cm^{-1}$) will constitute the Raman spectroscopic signature.

Raman signatures are sharp and narrow peaks observed on a Raman spectrum. These peaks are located on both sides of the excitation laser line (Stoke and anti-Stoke lines). Generally, only the Stokes region is used for comparison (the anti-Stoke region is identical in pattern, but much less intense) with a Raman spectrum of a known sample. A visual comparison of these set of peaks (spectroscopic signatures) between experimental and known samples is needed to verify the reproducibility of the data. Therefore, establishing correlations between experimental and known data is required to assign the peaks in the molecules, and identify a specific component in the sample.

The types of Raman spectroscopy suitable for use in conjunction with the present invention include but are not limited to conventional Raman spectroscopy, Raman microspectroscopy, near-field Raman spectroscopy, including but not limited to the tip-enhanced Raman spectroscopy, surface enhanced Raman spectroscopy (SERS) and surface enhanced resonance Raman spectroscopy (SERRS), coherent anti-Stokes Raman spectroscopy (CARS), etc. Also, both Stokes and anti-Stokes Raman spectroscopy could be used.

Another aspect of the present invention relates to a method of establishing reference Raman spectroscopic signatures for specific types of body fluids. This method involves providing known samples of specific types of body fluids. The known samples are subjected to Raman spectroscopy to produce a Raman spectroscopic signature for each known sample of a specific type of body fluid. A reference Raman spectroscopic signature is established for the specific type of body fluid based on the Raman spectroscopic signature obtained for each known sample of a specific type of body fluid subjected to Raman spectroscopy.

A further aspect of the present invention relates to a library of reference Raman spectroscopic signatures for different specific types of body fluids.

A library comprising different reference Raman spectroscopic signatures for different body fluids is realized in the present invention. The reference Raman spectroscopic signatures in the library include different species sources and different age ranges of specific body fluids.

In one embodiment of the present invention, the library comprises Raman spectroscopic signatures for human semen which has specific Raman wavenumbers of 640-643, 714-716, 828-830, 844-846, 954-959, 1002-1004, 1266-1269, 1326-1328, 1447-1450, and 1668-1670.

In another embodiment of the present invention, the library comprises Raman spectroscopic signatures for blood which has specific Raman wavenumbers of 741-747, 962-967, 1001-1002, 1121-1124, 1242-1248, 1335-1338, 1366-1368, 1444-1449, 1572-1576, and 1619-1620.

In another embodiment of the present invention, the library comprises Raman spectroscopic signatures for saliva which has specific Raman wavenumbers of 518-519, 619-620, 640-642, 850-852, 931-934, 1002-1003, 1124-1126, 1262-1268, 1445-1448, and 1651-1654.

In another embodiment of the present invention, the library comprises Raman spectroscopic signatures for vaginal fluid which has specific Raman wavenumbers of 526-530, 849-852, 932-935, 999-1001, 1078-1080, 1122-1124, 1205-1208, 1334-1337, 1443-1448, and 1650-1654.

In another embodiment of the present invention, the library comprises Raman spectroscopic signatures for sweat which has specific Raman wavenumbers of 527-533, 851-853, 998-1000, 1037-1040, 1082-1085, 1157-1161, 1414-1421, 1445-1451, 1592-1599, and 1667-1674.

In another embodiment of the present invention, the library comprises Raman spectroscopic signatures for canine semen which has specific Raman wavenumbers of 419-422, 520-523, 760-762, 839-841, 892-895, 954-957, 1062-1067, 1410-1414, 1465-1468, and 1604-1614.

EXAMPLES

The Examples set forth below are for illustrative purposes only and are not intended to limit, in any way, the scope of the present invention.

Example 1

Samples

The objective of this study is to preliminarily investigate the potential of NIR Raman spectroscopy for the identification of body fluids commonly found at crime scenes. The composition of body fluids varies substantially with its type as shown in Table 1. One hypothesis is that Raman spectroscopic signatures of the fluids should vary according to their composition and, consequently, should provide the basis for fluid identification. Reported here are individual NIR Raman spectra of dry traces of several body fluids including semen, vaginal fluid, saliva, sweat, and blood. Preliminary assignments of major Raman peaks were made based on literature data. In addition to comparing the five human body fluids, a sample of canine semen was compared to the human semen sample. It is also demonstrated that a mixture of fluids could be analyzed by fitting its Raman spectrum with a linear combination of Raman spectroscopic signatures of individual body fluids. It is important to emphasize that this preliminary study involved only one sample of each body fluid, and further research will be needed to characterize the variation of Raman spectroscopic signatures of body fluids acquired from different donors.

TABLE 1

Body Fluid Components

| Human Semen[1,2,3] | Canine Semen[4,5] | Vaginal Fluid[2,6,7] | Saliva[2,8] | Sweat[9] | Blood[2] |
|---|---|---|---|---|---|
| Albumin | Fructose | Urea | Lysozyme | Lactate | Hemoglobin |
| Fructose | Glucose | Lactate | Lipase | Urea | Albumin |
| Lysozyme | Lactate | Lysozyme | Amylase | | Fibrin |
| Lactate | Acid Phophatase | Acetic Acid | Thiocyanate | | Glucose |
| Urea | Lysozyme | Pyridine | Bicarbonate | | |
| Citric Acid | Citric Acid | | Phosphate | | |
| Ascorbic Acid | | | | | |

[1]Owen et al., J. Androl. 26: 459-469 (2005), which is hereby incorporated by reference in its entirety.
[2]In Wikipedia, The Free Encyclopedia, (Oct. 5, 2007), which is hereby incorporated by reference in its entirety.
[3]Family Beginnings, PC, Indianapolis, (2007), which is hereby incorporated by reference in its entirety.
[4]Chatterjee et al., Indian J. Exp. Biol. 14: 411-414 (1976), which is hereby incorporated by reference in its entirety.
[5]Bartlett, D. J., Nature 182: 1605-1606 (1958), which is hereby incorporated by reference in its entirety.
[6]Rajan et al., Infect. Immun. 67: 5027-5032 (1999), which is hereby incorporated by reference in its entirety.
[7]Wiberg-Itzel et al., Bjog. 113: 1426-1430 (2006), which is hereby incorporated by reference in its entirety.
[8]Farquharson et al., J. Raman Spectrosc. 36: 208-212 (2005), which is hereby incorporated by reference in its entirety.
[9]Mickelsen et al., J. Biol. Chem. 149: 479-490 (1943), which is hereby incorporated by reference in its entirety.

The fluids that were studied included human semen, vaginal fluid, saliva, sweat, and blood, as well as canine semen. The samples were obtained in liquid from both anonymous sources and volunteers. The blood sample was diluted ten times to reduce the intensity of the color and minimize the possibility of sample degradation due to absorption of the laser light. This was done because the dry traces of undiluted blood were too dark to be analyzed at 100% laser power. Partial lyophilization (Rey et al., *Freeze-drying/lyophilization of Pharmaceutical and Biological Products* (1999), which is hereby incorporated by reference in its entirety) was used to concentrate the saliva prior to drying. The vaginal fluid was slightly diluted with water to increase the volume of sample available to work with. Dry traces of sweat and semen were prepared from the original samples. Equal amounts of canine semen, vaginal fluid, and sweat were mixed and spotted onto a slide to dry for further analysis as a mixed sample.

A drop of each liquid sample was placed on a microscope slide that had been covered in aluminum foil to minimize fluorescence from the glass. The drops were allowed to dry completely, and Raman spectra were measured by direct illumination with the laser light without any cover. Several spectra of each sample were obtained from different spots within the dried drop to determine if there were any major visible changes throughout the sample. Each spectrum was an average of 10 scans accumulated for 10 seconds over a range of 100-3200 $cm^{-1}$.

Several standard solutions were also prepared for comparison to the fluid spectra. Solutions of about 140 mg/mL of urea, ascorbic acid, tyrosine, phenylalanine, lysozyme, and tryptophan were also measured as a dry trace on an aluminum slide, and these spectra were used in addition to the literature to identify component peaks in the fluid spectra.

Example 2

Raman Microscope

The 20× objective (numerical aperture of 0.40) of a Renishaw in Via confocal Raman spectrometer equipped with a research-grade Leica microscope and WiRE 2.0 software was used. A 785-nm laser light was utilized for excitation. The laser power on the sample was about 115 mW.

Example 3

Data Treatment

From the several spectra measured for each sample, the one with the least aluminum interference was chosen for comparison. GRAMS/AI 7.01 software was used for Raman spectra treatment. The contribution of aluminum was subtracted from each spectrum prior to the flat baseline correction.

A linear combination of Raman spectral signatures of individual body fluids was used for fitting the spectrum of an equal mixture of canine semen, human vaginal fluid, and sweat. MATLAB 7.4.0 software was used to do the fitting.

Example 4

General

Figure 1:
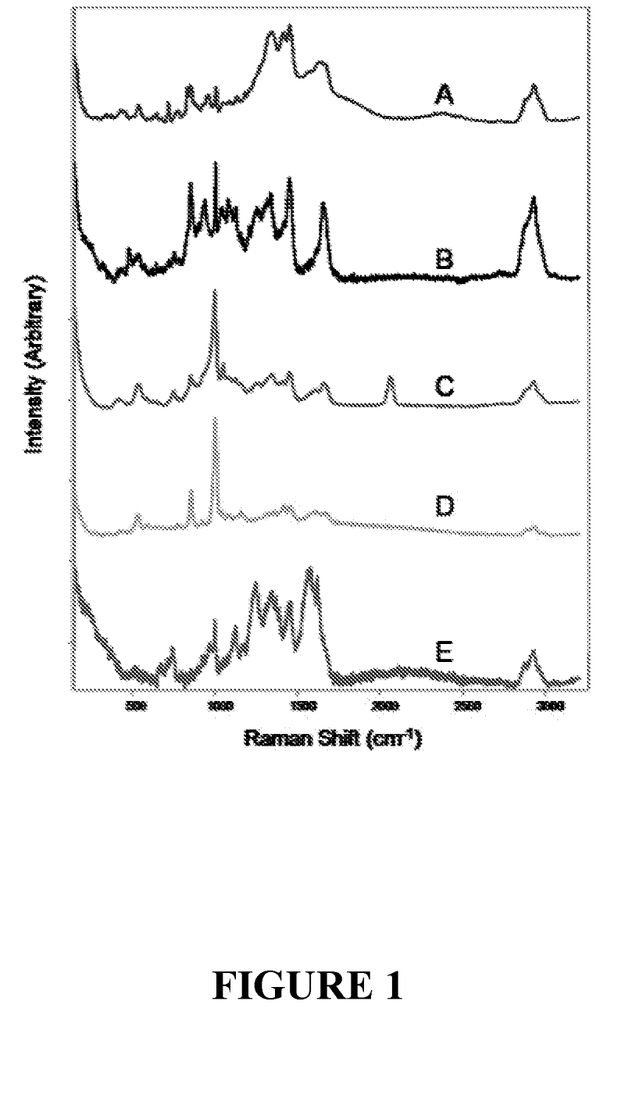
FIG. 1 illustrates the corrected Raman spectra of five pure human samples including a human semen (A), vaginal fluid (B), saliva (C), sweat (D), and blood (E).
Figure 2:
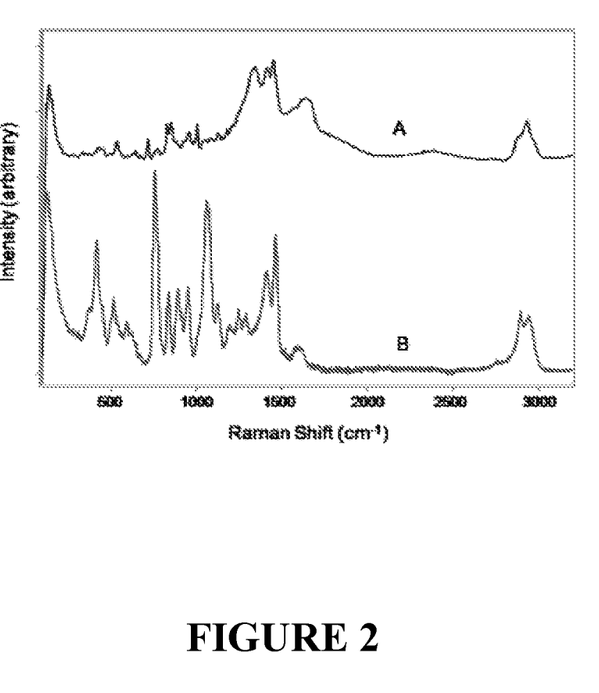
FIG. 2 illustrates comparative Raman spectra of human semen (A) and canine semen (B).

NIR Raman signatures of dried traces of individual human body fluids are shown in FIG. 1. Visual analysis showed that when several spectra were measured from different spots of the same sample, the only change that occurred was peak intensity variation due to the amount of background interference from the aluminum. The spectrum with the least interference was chosen for further analysis. It is easy to see that the spectra of all five body fluids are unique and can definitely be distinguished from one another by visual comparison alone. There are also several peaks that are common among the different fluids, and this is due to the fact that some of the fluids contain the same compounds (see Table 1). Preliminary vibrational mode assignments based on the literature data for each specific component are listed in Table 2.

TABLE 2

Peak Assignments For Fluids With Vibrational Modes

| Fluid | Raman Shift (cm$^{-1}$) | Vibrational Mode | Component |
|---|---|---|---|
| Human Semen | 536 | S—S stretch, symmetric skeletal vib.[1,2,3] | Lys, Lac, Urea |
| | 620 | CC aliphatic stretch[4,5] | Ascorbic Acid |
| | 831 | C—O—C symmetric stretch[4] | Fructose |
| | 853 | CC aliphatic stretch[2] | Tyr, Lac |
| | 960 | CC aliphatic stretch[4,6] | Citric Acid |
| | 1004 | Aromatic ring breathing, C—N stretch[3,4] | Phe, Urea |
| | 1342 | C—H bend[7] | Trp |
| | 1451 | $CH_2$, $CH_3$ bend[2,4] | Trp, Lac |
| | 1618 | $NH_2$ bend[3] | Urea |
| | 1662 | Amide I bend[1] | Lys |
| Canine Semen | 418 | CCO stretching[8] | Lac |
| | 760 | Ring vibrations[9] | Trp |
| | 1061 | C—O—C antisymmetric stretch[4,10] | Gluc., Fruc. |
| | 1126 | $CH_3$ rocking, C—O vibration[2] | Lac |
| | 1248 | Amide III bend[11] | Protein |
| | 1412 | $CH_2$, $CH_3$ bend[4,12] | Acid Phos. |
| | 1465 | $CH_2$, $CH_3$ bend[4,12] | Acid Phos. |
| Vaginal Fluid | 532 | Skeletal deformation[3] | Urea |
| | 641 | CC aliphatic stretch[13] | Acetic Acid |
| | 755 | Ring vibrations[9] | Trp |
| | 852 | CC aliphatic stretch[2] | Tyr, Lac |
| | 936 | CC aliphatic stretch[4,13] | Acetic Acid |
| | 1001 | Aromatic ring breathing, C—N stretch[3,4] | Phe, Urea |
| | 1043 | C—$CH_3$ vibration[2] | Lac |
| | 1082 | C—O vibration[2] | Lac |
| | 1125 | $CH_3$ rocking, C—O vibration[2] | Lac |
| | 1153 | $NH_3$ rocking[3] | Urea |
| | 1257 | Amide III bend[11] | Protein |
| | 1338 | C—H bend[7] | Trp |
| | 1447 | $CH_2$, $CH_3$ bend[2,4] | Trp, Lac |
| | 1664 | Amide I bend[1] | Lys |
| Saliva | 532 | S—S stretch[1] | Lys |
| | 749 | Ring vibrations[9] | Trp |
| | 851 | CC aliphatic stretch[4] | Tyr |
| | 1000 | Aromatic ring breathing[4] | Phe |
| | 1343 | C—H bend[7] | Trp |
| | 1449 | $CH_2$, $CH_3$ bend[4] | Trp |
| | 1660 | Amide I bend[1] | Lys |
| | 2060 | C—N stretch[14] | Thiocyanate |
| Sweat | 533 | Symmetric skeletal vibrations[2,3] | Lac, Urea |
| | 775 | $CO_2^-$ stretch[2] | Lac |
| | 853 | CC aliphatic stretch[2] | Lac |
| | 922 | $CH_3$ rocking[2] | Lac |
| | 1000 | Symmetric C—N stretch[3] | Urea |
| | 1041 | C—$CH_3$ vibration[2] | Lac |
| | 1084 | C—O vibration[2] | Lac |
| | 1158 | $NH_3$ rocking[3] | Urea |
| | 1452 | $CH_3$ bend[2] | Lac |
| | 1618 | $NH_2$ bend[2] | Urea |
| Blood | 742 | Ring vibrations[9] | Trp |
| | 1001 | Aromatic ring breathing[4] | Phe |
| | 1123 | C—O—C antisymmetric stretch[4] | Glucose |
| | 1247 | Amide III bend[11] | Protein |
| | 1341 | C—H bend[7] | Trp |
| | 1368 | $CH_3$ symmetric stretch[4,15] | Heme |

TABLE 2-continued

Peak Assignments For Fluids With Vibrational Modes

| Fluid | Raman Shift (cm$^{-1}$) | Vibrational Mode | Component |
|---|---|---|---|
| | 1446 | $CH_2$, $CH_3$ bend[4] | Trp |
| | 1576 | C═C stretch[16] | Heme |
| | 1619 | C═N stretch[4,16] | Heme |

[1] Chen et al., J. Am. Chem. Soc. 96: 3038-3042 (1974), which is hereby incorporated by reference in its entirety.
[2] Pecul et al., J. Phys. Chem. 106: 11008-11016 (2002), which is hereby incorporated by reference in its entirety.
[3] Fawcett et al., J. Raman Spectrosc. 3: 263-275 (1975), which is hereby incorporated by reference in its entirety.
[4] Grasselli, J., Chemical Applications of Raman Spectroscopy (1981), which is hereby incorporated by reference in its entirety.
[5] Dimension-P1 Raman System (2005), which is hereby incorporated by reference in its entirety.
[6] Silman et al., J. Phys. Chem. 87: 1014-1023 (1983), which is hereby incorporated by reference in its entirety.
[7] Johnson et al., J. Am. Chem. Soc. 108: 905-912 (1986), which is hereby incorporated by reference in its entirety.
[8] Kister et al., J. Raman Spectrosc. 26: 307-311 (1995), which is hereby incorporated by reference in its entirety.
[9] Aubrey et al., Biophys. J. 60: 1337-1349 (1991), which is hereby incorporated by reference in its entirety.
[10] Mathlouthi, M., Carbohydr. Res. 78: 225-233 (1980), which is hereby incorporated by reference in its entirety.
[11] Tuma et al., Proc. Natl. Acad. Sci. USA 95: 9885-9890 (1998), which is hereby incorporated by reference in its entirety.
[12] Twardowski et al., Biochim. Biophys. Acta 790: 70-77 (1984), which is hereby incorporated by reference in its entirety.
[13] Nakabayashi et al., J. Phys. Chem. 103: 8595-8603 (1999), which is hereby incorporated by reference in its entirety.
[14] Farquharson, et al., J. Raman Spectrosc. 36: 208-212 (2005), which is hereby incorporated by reference in its entirety.
[15] Hu et al., Biochemistry 36: 15701-15712 (1997), which is hereby incorporated by reference in its entirety.
[16] Sato et al., J. Biomed. Opt. 6: 366-370 (2001), which is hereby incorporated by reference in its entirety.

Example 5

Human Semen

The human semen spectrum (FIG. 1A) is composed of several different components including vibrational signatures of albumin, fructose, lysozyme, lactate, and urea (Owen et al., J. Androl, 26:459-469 (2005); In Wikipedia, The Free Encyclopedia, (Oct. 5, 2007); Family Beginnings, PC (2007), which are hereby incorporated by reference in their entirety). After comparison to reference spectra of albumin and lysozyme (Chen et al., J. Am. Chem. Soc. 96:3038-3042 (1974); Remmele et al., J. Protein Chem. 9:475-486 (1990), which are hereby incorporated by reference in their entirety), it was determined that these compounds contribute the most to the spectrum. There are also peaks present from urea and lactate as indicated in Table 2. The peak at 536 cm$^{-1}$ can be tentatively assigned to urea, lactate, and lysozyme. The complex nature of 536 cm$^{-1}$ and 1004 cm$^{-1}$ peaks is indicated by its different relative intensities in a pure urea spectrum measured with the same instrument and in the semen spectrum. Any slight discrepancies, which were found for the characteristic peak frequencies, between the body fluid spectra and the individual component spectra are most likely due to the environment created by the dry semen. Assignments for the smaller peaks were not made at this time.

Example 6

Vaginal Fluid

The pure spectrum of vaginal fluid (FIG. 1B) appears to be similar to the semen spectrum, but there are still substantial differences. The major components of vaginal fluid are urea, lactate, lysozyme, acetic acid, and pyridine (Rajan et al., Infect. Immun. 67:5027-5032 (1999); In Wikipedia, The Free Encyclopedia, (Oct. 5, 2007); Wiberg-Itzel et al., Bjog. 113:

1426-1430 (2006), which are hereby incorporated by reference in their entirety). Several reference spectra were used in determining the peak assignments (Weldon et al., *Appl. Spectrosc.* 52:265-269 (1998); Caspers et al., *Biophys. J.* 85:572-580 (2003); Bell et al., *Anal. Chem.* 70:332-339 (1998), which are hereby incorporated by reference in their entirety) including those from literature (Table 2) and the ones measured in applicants' laboratory using the same instrument. Lysozyme and urea peaks were common for both semen and vaginal fluid, and this is in agreement with the composition of these body fluids (Table 1). The peak around 1000 $cm^{-1}$ likely originates from urea and/or phenylalanine which is present in vaginal fluid proteins. Further quantitative analysis of the correlation between the fluid composition and the Raman spectrum is required to establish the species with dominating contribution to the Raman signal. Again, slight shifts in peak frequencies are observed when compared to the pure component spectra due to the dry vaginal fluid environment.

Example 7

Saliva

Saliva (FIG. 1C) contains many different components including amylase, lipase, and lysozyme (In *Wikipedia, The Free Encyclopedia*, (Oct. 5, 2007), which is hereby incorporated by reference in its entirety). Lysozyme (Chen et al., *J. Am. Chem. Soc.* 96:3038-3042 (1974); Remmele et al., *J. Protein Chem.* 9:475-486 (1990), which are hereby incorporated by reference in their entirety) contribution to the saliva Raman spectrum is evident through the peaks at 1343 $cm^{-1}$, 1449 $cm^{-1}$, and 1660 $cm^{-1}$, which match the corresponding peaks in semen and vaginal fluid also assigned to lysozyme. Both amylase (Stein et al., *J. Biol. Chem.* 235:371-378 (1960), which is hereby incorporated by reference in its entirety) and lipase (Bianchetta et al., *Eur. J. Biochem.* 97:395-405 (1979), which is hereby incorporated by reference in its entirety) contain phenylalanine in their sequences, and this amino acid results in a strong Raman peak at about 1000 $cm^{-1}$. The amide I vibrational mode of the polypeptide backbone (mainly C=O stretching vibration) is evident around 1660 $cm^{-1}$. A similar peak is present in the semen and vaginal fluid spectra. The peak at 2065 $cm^{-1}$ is very unique to saliva and is not present in any of the other fluids. The peak is likely caused by the presence of thiocyanate, which is commonly found in the saliva of a smoker. Thiocyanate is also found in smaller amounts in a non-smoker's saliva as an antibacterial agent (Farquharson, et al., *J. Raman Spectrosc.* 36:208-212 (2005), which is hereby incorporated by reference in its entirety).

Example 8

Sweat

The pure spectrum of sweat (FIG. 1D) is fairly simple like the saliva spectrum. This makes sense since it has fewer major components than semen or vaginal fluid and is dominated by lactic acid and urea (Mickelsen et al., *J. Biol. Chem.* 149:479-490 (1943), which is hereby incorporated by reference in its entirety). Urea is the largest contributor, and this peak at 1000 $cm^{-1}$ can be compared to every other body fluid spectrum. It has the same Raman shift as phenylalanine in proteins. A previous study involving sweat ducts (Caspers et al., *Biophys. J.* 85:572-580 (2003), which is hereby incorporated by reference in its entirety) reveals a comparable Raman spectrum of sweat to the results stated here, and that study was used to assign major peaks in addition to other sources (Pecul et al., *J. Phys. Chem.* 106:11008-11016 (2002), which is hereby incorporated by reference in its entirety). No other minor components were assigned at this time.

Example 9

Blood Sample Preparation

A set of fifty (50) samples of bloodstains on paper were obtained from the New York State Forensic Investigation Center. Each sample was from a different donor, and visual observation indicated that each stain had varying amounts of blood contribution. Each sample was measured using automatic mapping that scanned a sample area of A×B μm and measured Raman spectra from 32 evenly spaced points within the area with two (2) ten-second accumulations at each point. The laser power was reduced to 10% to avoid sample photodegradation. A paper control sample was also provided, and its Raman spectrum was measured under the same conditions as the bloodstains The whole blood sample was obtained from an anonymous donor, and the dried sample was prepared for measurement by placing a small drop on a piece of aluminum foil placed on a circular glass slide designed for the automatic mapping stage. The foil helped removed the fluorescence interference from the glass. The drop was allowed to dry completely, and the same A×B sample area was scanned as before with Raman spectra being measured from 16 points with fifteen (15) ten-second accumulations at each point with 10% laser power. The liquid sample was prepared by placing a drop of blood on a piece of aluminum foil on a circular glass slide and immediately measuring only one spectrum with fifteen (15) ten-second accumulations. Automatic mapping was not used since the components of liquid blood were not determined at this time.

Pure samples of semen and saliva were also obtained anonymously for analysis and subsequent comparison to the bloodstain data. These fluids were prepared by placing a drop on a piece of aluminum foil covering a slide. The drop was allowed to dry completely, and the spectra were measured with 100% laser power for ten (10) ten-second accumulations. No automatic mapping was used for these samples since only one spectrum was needed for comparison purposes.

Example 10

Blood

The Raman spectrum of blood (FIG. 1E) has several contributing components including hemoglobin, albumin, and glucose (In *Wikipedia, The Free Encyclopedia*, (Oct. 5, 2007), which is hereby incorporated by reference in its entirety). Hemoglobin is the major contributor since it contributes to 95% of the dried weight of red blood cells (In *Encyclopaedia Britannica Online* (Oct. 5, 2007), which is hereby incorporated by reference in its entirety). Reference spectra of hemoglobin (Spiro et al., *Proc. Natl. Acad. Sci. USA* 69:2622-2626 (1972); Hu et al., *Biochemistry* 36:15701-15712 (1997), which are hereby incorporated by reference in their entirety) were used to make the assignments on the blood Raman spectrum. Again, the 1001 $cm^{-1}$ peak is due to the presence of phenylalanine in albumin (Dugaiczyk et al., *Proc. Natl. Acad. Sci. USA* 79:71-75 (1982), which is hereby incorporated by reference in its entirety) similar to the phenylalanine containing proteins, lipase and amylase, in saliva. The amide II vibrational mode, which consists of C—N stretching, N—H bending, and C—C stretching (Topilina et al., *Biopolymers* 86:261-264 (2007), which is hereby incorporated by reference in its entirety), is evident at 1247 cm$^{-1}$ (Tuma et al., *Proc. Natl. Acad. Sci. USA* 95:9885-9890 (1998), which is hereby incorporated by reference in its entirety).

Example 11

Bloodstains

Figure 4:
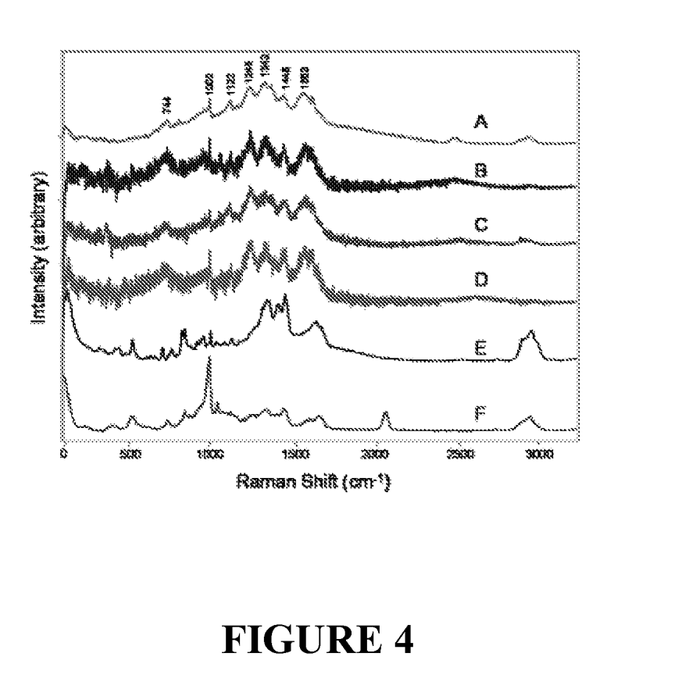
FIG. 4 shows the spectra of pure dried blood (A), the three blood components of three donors extracted from the stains (B-D), dried semen (E), and dried saliva (F).

Three blood component spectra extracted from bloodstains of three different donors along with a spectrum of pure dried blood, semen, and saliva are examined (FIG. 4). Major peaks for this analysis are labeled as well as their assignments listed in Table 3. The nature of the statistical analysis causes the component spectra to have lower resolution in comparison to the pure spectra, but major peaks can still be identified and are comparable to the spectrum of pure blood. It is obvious from visual comparison that the component spectra match the pure blood spectrum and differ from the semen and saliva spectra. The dried blood and blood components all share the unique major peaks of 1248 and 1563 cm$^{-1}$ that are not present in either semen or saliva. These peaks are the result of the amide III bending mode of hemoglobin (Sato et al., "Excitation Wavelength-Dependent Changes in Raman Spectra of Whole Blood and Hemoglobin: Comparison of the Spectra with 514.5-, 720-, and 1064-nm Excitation," *J. Biomed. Opt.* 6:366-70 (2001), which is hereby incorporated by reference in its entirety) and the C═C stretching in heme (Sato et al., "Excitation Wavelength-Dependent Changes in Raman Spectra of Whole Blood and Hemoglobin: Comparison of the Spectra with 514.5-, 720-, and 1064-nm Excitation," *J. Biomed. Opt.* 6:366-70 (2001), which is hereby incorporated by reference in its entirety), respectively. Some common peaks among all three fluids are 1000 cm$^{-1}$ and 1448 cm$^{-1}$ which are the result of phenylalanine and tryptophan, respectively. Despite some peak similarities, the relative intensity of each peak is different for each fluid and allows the stain components to be identified as blood and not semen or saliva. Data from only three bloodstains is reported here at this time, but the analysis was performed on the majority of the available samples with similar results. This preliminary data demonstrates the ability of NIR Raman spectroscopy to identify the presence of blood in an unknown body fluid stain and distinguishes it from other body fluids commonly found at crime scenes. This non-destructive technique is a valuable alternative to other destructive presumptive and confirmatory tests for blood.

TABLE 3

Raman Assignments of Dried Blood

| Raman Shift of Dried Blood (cm-1) | Vibrational Mode | Components |
|---|---|---|
| 744 | Ring Vibrations | Trp |
| 967 | Uncertain | Hemoglobin [venkatesh] |
| 1000 | Aromatic Ring Breathing | Phe [venkatesh] |
| 1122 | C—C Symmetrical Stretch | Heme [Ozaki] |
| 1248 | Amide III Bend | Hemoglobin |
| 1342 | C—H Bend | Trp |
| 1368 | CH3 Symmetric Stretch | Heme |
| 1448 | CH2, CH3 bend | Trp [Ozaki] |
| 1542 | C═C Stretch | Heme [Ozaki] |

TABLE 3-continued

Raman Assignments of Dried Blood

| Raman Shift of Dried Blood (cm-1) | Vibrational Mode | Components |
|---|---|---|
| 1563 | Pyrrole Ring C—C Stretching | Hemoglobin [Cho] |
| 1575 | C═C Stretch | Heme |
| 1620 | C═C Stretch | Heme [Ozaki] |

Example 12

Dried Blood and Liquid Blood

Figure 5:
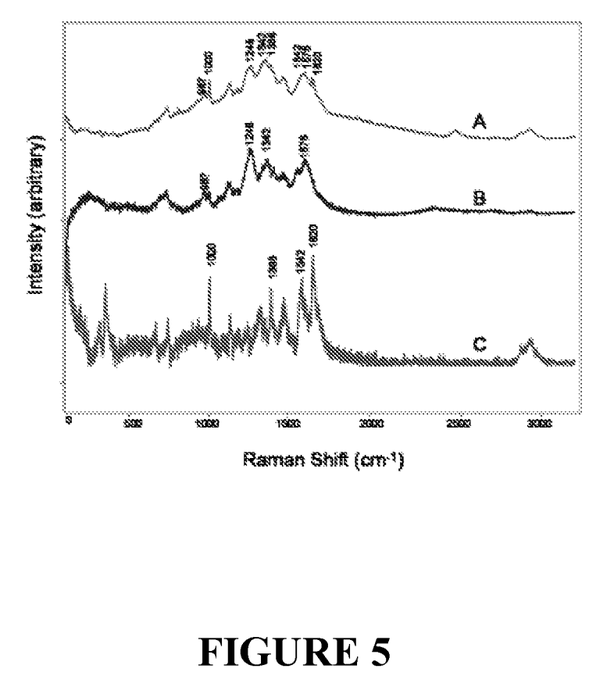
FIG. 5 illustrates the spectra of dried blood (A) along with component 1 (B) and component 2 (C) found through statistical analysis.

The spectrum of dried blood along with the two components extracted from statistical analysis is examined as illustrated in FIG. 5. Major peaks are labeled to illustrate which components are contributing to specific peaks of the dried blood. Some peaks in the blood spectrum are a combination of both components. Component 1 was found to be the major component, and component 2 was the minor. Comparison to literature data (Sato et al., "Excitation Wavelength-Dependent Changes in Raman Spectra of Whole Blood and Hemoglobin: Comparison of the Spectra with 514.5-, 720-, and 1064-nm Excitation," *J. Biomed. Opt.* 6:366-70 (2001), which is hereby incorporated by reference in its entirety) reveals that component 2 is similar to hemoglobin due to the presence of peaks around 1000, 1368, 1542, and 1620 cm$^{-1}$ in the component. Hemoglobin contributes to 97% of dried blood, so it is expected that hemoglobin would be one of the principle components found through statistical analysis. It is believed that component 1 is coming from the protein fibrin. Fibrin is formed during the blood clotting process and can be found in a large concentration in the dried blood. Only a small amount of literature data on the Raman spectrum of fibrin is available, but some of the unique peaks such as 967, 1248, and 1342 cm$^{-1}$ in component 1 are similar to major peaks of pure fibrin and further suggest that this major component of the dried blood is in fact fibrin.

Figure 6:
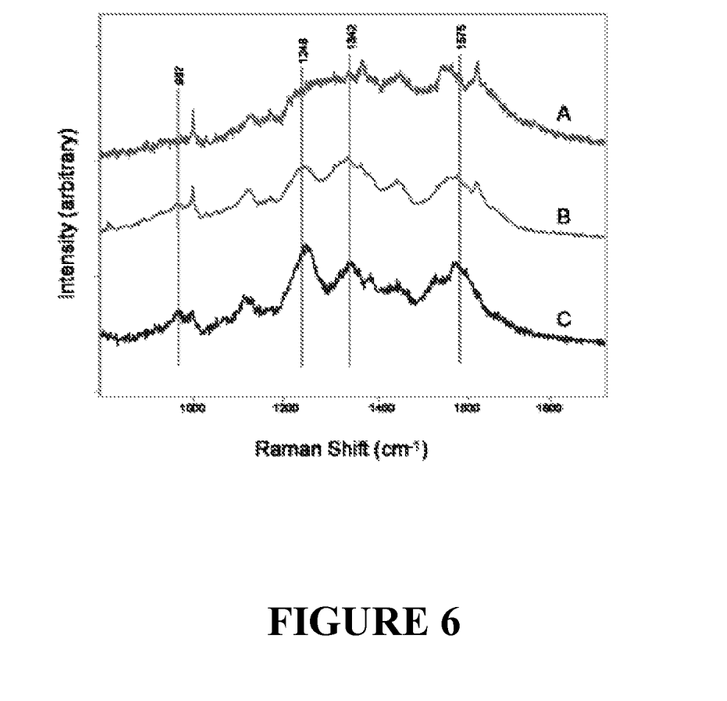
FIG. 6 illustrates the enhanced spectra of liquid blood (A), dried blood (B), and component 1 from the dried blood (C).

The enhanced spectra of liquid blood, dried blood, and component 1 are shown in FIG. 6. The main differences between the liquid blood and dried blood are marked and labeled, and these peaks match the major peaks of component 1. Peaks at 967, 1248, 1342, and 1575 cm$^{-1}$ in component 1 contribute to the changes that occur between the liquid and dried blood spectra. This figure illustrates that Raman spectroscopy can identify the changes that occur in a blood sample as it dries, and it also shows that component 1 is formed as blood dries. Knowing the identities of the principle components in a blood sample will help identify and confirm the presence of blood in an unknown stain and distinguish it from other body fluids.

Example 13

Raman Signature of Human and Canine Semen

Canine and human semen Raman spectra (FIG. 1) contain many similar characteristic bands, yet the spectra exhibit striking differences evident even to a naked eye. These include different relative intensities of peaks common to both spectra as well as certain bands present in one of these spectra only. For example, the very strong peak at 760 cm$^{-1}$ in the canine spectrum is due to the presence tryptophan in an undetermined protein (Aubrey et al., *Biophys. J.* 60:1337-1349

(1991), which is hereby incorporated by reference in its entirety), and this protein is present in the human sample in a lower concentration. Another peak at 1061 cm$^{-1}$ from a combination of glucose and fructose (Mathlouthi, M., *Carbohydr. Res.* 78:225-233 (1980), which is hereby incorporated by reference in its entirety) is very strong in the canine sample and barely evident in the human sample. The human sample shows higher contribution from lactate based on the larger relative intensities of the 536 cm$^{-1}$, 829 cm$^{-1}$, and 1452 cm$^{-1}$ peaks. Some peaks that appear to be unique to the canine spectrum are 1248 cm$^{-1}$ and 418 cm$^{-1}$. The human spectrum is unique with peaks at 1342 cm$^{-1}$, 1004 cm$^{-1}$, and 536 cm$^{-1}$. Ultimately, the ability to quickly distinguish between animal and human body fluids will be very useful in forensic analysis both in the laboratory and at the crime scene.

Example 14

Mixture

Figure 3:
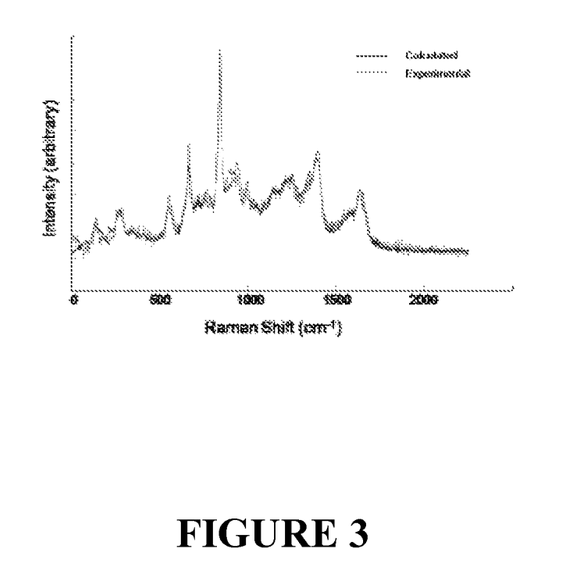
FIG. 3 illustrates the experimental and calculated Raman spectra of mixed sample of three body fluids.

The canine semen, human vaginal fluid, and sweat were randomly chosen for the mixture. Many other combinations of body fluids are possible, but this was the only one explored at this time. The experimental and calculated mixture spectra are shown in FIG. 3. The best liner combination of three pure spectra of the individual components was found to fit to the experimental Raman spectrum of the mixed sample using MATLAB 7.4.0. One can appreciate a good quality fitting (FIG. 3) although the quantitative analysis of the fit and the evaluation of the mixture composition based on the Raman spectroscopic measurement is the subject of ongoing investigation.

The ability to distinguish dry traces of all body fluids from each other in a non-destructive manner is demonstrated using near-IR Raman spectroscopy. Taking into account a general composition of each fluid preliminarily allows the assignment of major Raman spectroscopic features. A distinct difference between Raman spectra of human and canine semen indicates a great potential of Raman spectroscopy for distinguishing body fluids of human and animal origin. In addition, it is shown that a mixture of body fluids could be easily fit with a linear combination of individual fluid spectra. This preliminary study utilizes one sample of each body fluid including human semen, vaginal fluid, sweat, saliva, blood, and canine semen. Further investigation of the variation in Raman spectroscopic signatures of each body fluid is underway. Furthermore, work on the development of a statistical method for quantitative determination of the mixed sample composition is based on Raman spectroscopy.

The use of this technique is envisioned for nondestructive detection and confirmatory identification of body fluids at a crime scene. A crime scene investigator would be able to determine the fluid's identity and whether if it was pure and not contaminated. In the case of a mixed sample, the composition of the mixture could also be determined at this point in time, as well as the human or animal nature of the fluids. The ability to make these determinations and identifications, especially on site at a crime scene, would be a major step in the area of forensic analysis of body fluids. In addition, the ability to make these conclusions without damaging the sample would be invaluable due to the ability to conduct further testing.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of identifying types of body fluids in a sample, said method comprising:
   providing a sample potentially containing one or more types of body fluids;
   subjecting the sample to Raman spectroscopy to produce a Raman spectroscopic signature for the sample; and
   identifying the Raman spectroscopic signature to ascertain the types of body fluids in the sample.

2. The method of claim 1, wherein the body fluid is selected from the group consisting of blood, semen, saliva, vaginal fluid, sweat, canine semen, and combinations thereof.

3. The method of claim 1, wherein the sample is a solid or liquid.

4. The method of claim 1, wherein said identifying comprises:
   comparing the Raman spectroscopic signature for the sample to reference Raman spectroscopic signatures for different body fluids and
   determining the type of body fluids in the sample based on said comparing.

5. The method of claim 1, wherein said identifying determines the species source of the body fluid in the sample.

6. The method of claim 5, wherein said identifying distinguishes a human body fluid from an animal body fluid.

7. The method of claim 1, wherein said identifying determines the age range of the source of the body fluid in the sample.

8. The method of claim 4, wherein the body fluid is selected from the group consisting of blood, semen, saliva, vaginal fluid, sweat, canine semen, and combinations thereof.

9. The method of claim 8, wherein the reference Raman spectroscopic signature is for human semen which comprises specific Raman wavenumbers of 640-643, 714-716, 828-830, 844-846, 954-959, 1002-1004, 1266-1269, 1326-1328, 1447-1450, and 1668-1670 cm$^{-1}$.

10. The method of claim 8, wherein the reference Raman spectroscopic signature is for blood which comprises specific Raman wavenumbers of 741-747, 962-967, 1001-1002, 1121-1124, 1242-1248, 1335-1338, 1366-1368, 1444-1449, 1572-1576, and 1619-1620 cm$^{-1}$.

11. The method of claim 8, wherein the reference Raman spectroscopic signature is for saliva which comprises specific Raman wavenumbers of 518-519, 619-620, 640-642, 850-852, 931-934, 1002-1003, 1124-1126, 1262-1268, 1445-1448, and 1651-1654 cm$^{-1}$.

12. The method of claim 8, wherein the reference Raman spectroscopic signature is for vaginal fluid which comprises specific Raman wavenumbers of 526-530, 849-852, 932-935, 999-1001, 1078-1080, 1122-1124, 1205-1208, 1334-1337, 1443-1448, and 1650-1654 cm$^{-1}$.

13. The method of claim 8, wherein the reference Raman spectroscopic signature is for sweat which comprises specific Raman wavenumbers of 527-533, 851-853, 998-1000, 1037-1040, 1082-1085, 1157-1161, 1414-1421, 1445-1451, 1592-1599, and 1667-1674 cm$^{-1}$.

14. The method of claim 8, wherein the reference Raman spectroscopic signature is for canine semen which comprises specific Raman wavenumbers of 419-422, 520-523, 760-762, 839-841, 892-895, 954-957, 1062-1067, 1410-1414, 1465-1468, and 1604-1614 cm$^{-1}$.

15. The method of claim 1, wherein the type of body fluid in the sample is unknown.

16. The method of claim 1, wherein said method is carried out as a confirmatory test.

17. The method of claim 1, wherein said method is carried out to distinguish one body fluid from another body fluid.

18. The method of claim 1, wherein the sample is from a crime scene.

19. The method of claim 1, wherein the sample comprises an individual body fluid.

20. The method of claim 1, wherein the sample comprises a mixture of body fluids.

* * * * *